US007674864B2

(12) United States Patent
Zoromski et al.

(10) Patent No.: US 7,674,864 B2
(45) Date of Patent: Mar. 9, 2010

(54) POLYMERIC HYBRID PRECURSORS, POLYMERIC HYBRID PRECURSOR COMPOSITE MATRICES, MEDICAL DEVICES, AND METHODS

(75) Inventors: Michele L. Zoromski, Minneapolis, MN (US); Liliana L. Atanasoska, Edina, MN (US); Scott R. Schewe, Eden Prairie, MN (US); Robert W. Warner, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 538 days.

(21) Appl. No.: 11/317,613

(22) Filed: Dec. 23, 2005

(65) Prior Publication Data

US 2007/0149743 A1 Jun. 28, 2007

(51) Int. Cl.
*C08L 71/02* (2006.01)
(52) U.S. Cl. .......................... 525/403; 525/55; 528/901
(58) Field of Classification Search ................. 525/403, 525/55; 528/901
See application file for complete search history.

(56) References Cited

U.S. PATENT DOCUMENTS

| 2,928,858 | A | 3/1960 | Morehouse |
| 4,780,337 | A | 10/1988 | Seyferth et al. |
| 5,180,757 | A | 1/1993 | Lucey |
| 5,254,744 | A | 10/1993 | Neumer |
| 5,316,695 | A | 5/1994 | Wilkes et al. |
| 5,389,170 | A | 2/1995 | Brady et al. |
| 5,486,565 | A | 1/1996 | Gentle et al. |
| 5,665,823 | A | 9/1997 | Saxena et al. |
| 5,681,872 | A | 10/1997 | Erbe |
| 5,716,565 | A | 2/1998 | Stangle et al. |
| 5,834,007 | A | 11/1998 | Kubota |
| 5,854,298 | A | 12/1998 | McNay et al. |
| 5,871,777 | A | 2/1999 | Ducheyne et al. |
| 5,874,109 | A | 2/1999 | Ducheyne et al. |
| 5,914,356 | A | 6/1999 | Erbe |
| 6,001,522 | A | 12/1999 | Woo et al. |
| 6,039,897 | A | 3/2000 | Lochhead et al. |
| 6,069,259 | A | 5/2000 | Crivello |
| 6,103,033 | A | 8/2000 | Say et al. |
| 6,120,676 | A | 9/2000 | Heller et al. |
| 6,131,580 | A | 10/2000 | Ratner et al. |
| 6,134,461 | A | 10/2000 | Say et al. |
| 6,143,164 | A | 11/2000 | Heller et al. |
| 6,162,611 | A | 12/2000 | Heller et al. |
| 6,175,752 | B1 | 1/2001 | Say et al. |
| 6,210,790 | B1 | 4/2001 | Crivello |
| 6,214,530 | B1 | 4/2001 | Morrison et al. |
| 6,251,260 | B1 | 6/2001 | Heller et al. |
| 6,280,838 | B1 | 8/2001 | Bernards et al. |
| 6,281,322 | B1 | 8/2001 | Groth et al. |
| 6,284,478 | B1 | 9/2001 | Heller et al. |
| 6,299,757 | B1 | 10/2001 | Feldman et al. |
| 6,303,290 | B1 | 10/2001 | Liu et al. |
| 6,323,146 | B1 | 11/2001 | Pugh et al. |
| 6,329,161 | B1 | 12/2001 | Heller et al. |
| 6,338,790 | B1 | 1/2002 | Feldman et al. |
| 6,368,535 | B1 | 4/2002 | Katsoulis et al. |
| 6,391,999 | B1 | 5/2002 | Crivello |
| 6,413,538 | B1 | 7/2002 | Garcia et al. |
| 6,448,331 | B1 | 9/2002 | Ioka et al. |
| 6,458,386 | B1 | 10/2002 | Schacht et al. |
| 6,461,496 | B1 | 10/2002 | Feldman et al. |
| 6,465,387 | B1 | 10/2002 | Pinnavaia et al. |
| 6,479,565 | B1 | 11/2002 | Stanley |
| 6,484,046 | B1 | 11/2002 | Say et al. |
| 6,506,921 | B1 * | 1/2003 | Wilkes et al. ............... 556/413 |
| 6,514,718 | B2 | 2/2003 | Heller et al. |
| 6,548,590 | B1 | 4/2003 | Koloski et al. |
| 6,551,494 | B1 | 4/2003 | Heller et al. |
| 6,555,175 | B2 | 4/2003 | Johnson |
| 6,565,509 | B1 | 5/2003 | Say et al. |
| 6,566,456 | B1 | 5/2003 | Yang et al. |
| 6,576,101 | B1 | 6/2003 | Heller et al. |
| 6,585,992 | B2 | 7/2003 | Pugh et al. |

(Continued)

FOREIGN PATENT DOCUMENTS

WO     WO 99/21654 A1     5/1999

(Continued)

OTHER PUBLICATIONS

XP-002443403 Nunes, S.C., et al. "Structure and Photoluminescent features of di-amide cross-linked alkylene-siloxane hybrids", J. Mater. Chem., vol. 15, pp. 3876-3886 (2005).

(Continued)

*Primary Examiner*—Kuo-Liang Peng
(74) *Attorney, Agent, or Firm*—Brooks, Cameron & Huebsch, PLLC

(57) ABSTRACT

Polymeric hybrid precursors, mixtures of polymeric hybrid precursors and polymers, and polymer composite matrices prepared from the mixture of the polymeric hybrid precursors and the polymer. The mixture of the polymeric hybrid precursors and the polymer can undergo a process to form the polymer composite matrix having a cross-linked network of a silasesquioxane based polymer formed from the polymeric hybrid precursors that interpenetrates the polymer. The polymeric hybrid precursors include chemical linkage moieties that are capable of forming non-covalent bonds with portions of the polymer. The polymer composite matrices are useful as biomaterials in medical devices.

8 Claims, No Drawings

U.S. PATENT DOCUMENTS

| | | |
|---|---|---|
| 6,591,125 B1 | 7/2003 | Buse et al. |
| 6,592,745 B1 | 7/2003 | Feldman et al. |
| 6,599,631 B2 | 7/2003 | Kambe et al. |
| 6,616,819 B1 | 9/2003 | Liamos et al. |
| 6,618,934 B1 | 9/2003 | Feldman et al. |
| 6,620,905 B1 | 9/2003 | Musa |
| 6,645,644 B1 | 11/2003 | Schwartz et al. |
| 6,649,083 B1 | 11/2003 | Pinnavaia et al. |
| 6,649,713 B2 | 11/2003 | Tang et al. |
| 6,654,625 B1 | 11/2003 | Say et al. |
| 6,667,016 B1 | 12/2003 | Meyer et al. |
| 6,749,740 B2 | 6/2004 | Liamos et al. |
| 6,759,431 B2 | 7/2004 | Hunter et al. |
| 6,828,404 B2 | 12/2004 | Crivello |
| 6,841,601 B2 | 1/2005 | Serpico et al. |
| 6,846,493 B2 | 1/2005 | Pugh et al. |
| 6,869,938 B1 | 3/2005 | Schwartz et al. |
| 6,881,551 B2 | 4/2005 | Heller et al. |
| 6,884,628 B2 | 4/2005 | Hubbell et al. |
| 6,916,640 B2 | 7/2005 | Yu et al. |
| 6,942,518 B2 | 9/2005 | Liamos et al. |
| 6,955,771 B2 | 10/2005 | Ryang |
| 6,973,706 B2 | 12/2005 | Say et al. |
| 6,975,893 B2 | 12/2005 | Say et al. |
| 7,003,340 B2 | 2/2006 | Say et al. |
| 2002/0042657 A1 | 4/2002 | Pugh et al. |
| 2002/0094569 A1 | 7/2002 | Yu et al. |
| 2002/0123592 A1 | 9/2002 | Zhang et al. |
| 2002/0128234 A1 | 9/2002 | Hubbell et al. |
| 2002/0192289 A1 | 12/2002 | Zheng et al. |
| 2002/0197456 A1 | 12/2002 | Pope |
| 2002/0197467 A1 | 12/2002 | Johnson |
| 2003/0003160 A1 | 1/2003 | Pugh et al. |
| 2003/0044802 A1 | 3/2003 | Sayler et al. |
| 2003/0055139 A1 | 3/2003 | Cruse |
| 2003/0062263 A1 | 4/2003 | Stanford et al. |
| 2003/0065121 A1 | 4/2003 | Lee |
| 2003/0118887 A1 | 6/2003 | Serpico et al. |
| 2003/0158351 A1 | 8/2003 | Smith, Jr. et al. |
| 2003/0199615 A1 | 10/2003 | Chaput et al. |
| 2003/0236573 A1 | 12/2003 | Evans et al. |
| 2004/0001959 A1 | 1/2004 | Schwartz et al. |
| 2004/0009598 A1 | 1/2004 | Hench et al. |
| 2004/0023048 A1 | 2/2004 | Schwartz et al. |
| 2004/0034434 A1 | 2/2004 | Evans et al. |
| 2004/0053060 A1 | 3/2004 | Roziere et al. |
| 2004/0064193 A1 | 4/2004 | Evans et al. |
| 2004/0121451 A1 | 6/2004 | Moritz et al. |
| 2004/0127987 A1 | 7/2004 | Evans et al. |
| 2004/0137582 A1 | 7/2004 | Dordick et al. |
| 2004/0138758 A1 | 7/2004 | Evans et al. |
| 2004/0150331 A1 | 8/2004 | Okubo et al. |
| 2004/0172061 A1 | 9/2004 | Yoshioka et al. |
| 2004/0249082 A1 | 12/2004 | Zhang et al. |
| 2004/0258726 A1 | 12/2004 | Stupp et al. |
| 2005/0010001 A1 | 1/2005 | Reddy et al. |
| 2005/0032246 A1 | 2/2005 | Brennan et al. |
| 2005/0038220 A1 | 2/2005 | Shin et al. |
| 2005/0038498 A1 | 2/2005 | Dubrow et al. |
| 2005/0043894 A1 | 2/2005 | Fernandez |
| 2005/0100578 A1 | 5/2005 | Schmid et al. |
| 2005/0124243 A1 | 6/2005 | Patel et al. |
| 2005/0163821 A1 | 7/2005 | Sung et al. |
| 2005/0201987 A1 | 9/2005 | Pirhonen et al. |
| 2005/0215728 A1 | 9/2005 | Cao et al. |
| 2005/0220891 A1 | 10/2005 | Yu et al. |
| 2005/0221072 A1 | 10/2005 | Dubrow et al. |
| 2005/0226904 A1 | 10/2005 | Choi et al. |
| 2005/0231773 A1 | 10/2005 | Sasa et al. |
| 2005/0237483 A1 | 10/2005 | Phelan |
| 2005/0238080 A1 | 10/2005 | Wolkin et al. |
| 2006/0025524 A1 | 2/2006 | Schneider et al. |
| 2006/0029811 A1 | 2/2006 | Sugioka et al. |

FOREIGN PATENT DOCUMENTS

| | | |
|---|---|---|
| WO | WO 02/46130 | 6/2002 |
| WO | WO 2004/022121 | 3/2004 |
| WO | WO 2004/024201 | 3/2004 |
| WO | WO 2004/099068 | 11/2004 |
| WO | WO 2004/103319 | 12/2004 |
| WO | WO 2005/047467 | 5/2005 |
| WO | WO 2005/082277 | 9/2005 |
| WO | WO 2005/084582 | 9/2005 |

OTHER PUBLICATIONS

International Search Report (8 pgs.).

Honma, "Synthesis of organic/inorganic nanocomposites protonic conducting membrane through sol-gel processes", Solid State Ionics, 1999, vol. 118, pp. 29-36.

Honma,"Protonic conducting properties of sol-gel derived organic/inorganic nanocomposite membranes doped with acidic functional molecules",Solid St. Ionics,1999,v.120,p. 255-264.

Honma, "Protonic organic/inorganic nanocomposites for polymer electrolyte membrane", Journal of Membrane Science, 2001, vol. 185, pp. 83-94.

Huang, "Structure-property behaviour of hybrid materials incorporating tetraethoxysilane with multifunctional poly(tetramethylene oxide)",Polymer,Nov. 1989,vol. 30, p. 2001-2012.

Young, "Covalent and non-covalently coupled polyester-inorganic composite materials", Polymer, 2002, vol. 43, pp. 6101-6114.

Bermudez, "Sol-gel derived urea cross-linked organically modified silicates. 1. room termperature mid-infrared spectra", Chem. Mater., 1999, vol. 11, pp. 569-580.

Yano, "Physical properties and structure of organic-inorganic hybrid materials produced by sol-gel process", Materials Science & Engineering, 1998, vol. 6, pp. 75-90.

Correia, "Sol-gel-derived POE/siliceous hybrids doped with Na+ ions: morphology and ionic conductivity", Solid State Ionics, 2003, vol. 156, pp. 85-93.

Bounor-Legare, "New transesterification between ester and alkoxysilane groups:application to ethylene-co-vinyl acetate copolymer crosslinking",Polymer,2002,vol. 43, p. 6085-6092.

Bounor-Legare, "A new route for organic-inorganic hybrid material synthesis through reactive processing without solvent", Polymer, 2004, vol. 45, pp. 1485-1493.

* cited by examiner

_US 7,674,864 B2_

POLYMERIC HYBRID PRECURSORS, POLYMERIC HYBRID PRECURSOR COMPOSITE MATRICES, MEDICAL DEVICES, AND METHODS

FIELD OF THE DISCLOSURE

The present disclosure relates to polymeric hybrid precursors having both organic and inorganic groups, a mixture of the polymeric hybrid precursors and a polymer where the polymeric hybrid precursors are capable of forming an interpenetrating network through the polymer, and polymer composite matrices prepared from the mixture of the polymeric hybrid precursors and the polymer. The polymer composite matrices are useful as biomaterials in medical devices.

BACKGROUND OF THE DISCLOSURE

Biomaterials research involves many areas of material science. The area of material science generally depends on the intended application of the biomaterial. For example, metals and metal alloys are used in orthopedics, dentistry and other load bearing applications; ceramics are used because of their chemically inert nature or their high bioactivity; polymers are used for soft tissue replacement and used for many other non-structural applications.

Regardless of their application, biomaterials are often required to maintain a balance between application specific mechanical properties and their biological effect on the body. So, biomaterial are often required to display a range of properties, such as biological activity (or inactivity), mechanical strength, chemical durability, etc. These aspects of biomaterial design are important to the successful application of the biomaterial to a given situation and/or application. Use of composite technology has enabled biomedical material researchers to develop a wide range of new biocomposites, which offer the promise to improve the quality of life of many people.

In a specific example, attempts have been made to incorporate ceramic and/or metallic nanoparticles into polymer matrices for the purpose of improving both the durability and surface characteristics (e.g., abrasion resistance) of polymers. However, the ceramic and/or metallic nanoparticles tend to conglomerate or clump when processed or mixed into the base polymer material. A suitable solution to this problem is desired.

DETAILED DESCRIPTION OF DISCLOSURE

The present disclosure provides a polymeric hybrid precursor having both organic and inorganic groups, a mixture of the polymeric hybrid precursor and a polymer where the polymeric hybrid precursor is capable of forming an interpenetrating network through the polymer, and polymer composite matrices prepared from the mixture of the polymeric hybrid precursor and the polymer. The mixture of the polymeric hybrid precursor and the polymer, according to the present disclosure, can be mixed so as to remain miscible throughout the processing steps. According to the present disclosure, the polymeric hybrid precursor can include chemical linkage moieties capable of forming non-covalent bonds with portions of the polymer. The resulting mixture of the polymeric hybrid precursor in the polymer can be processed into a desired shape. The resulting mixture having the desired shape can then undergo a sol-gel process to form the polymer composite matrix having a cross-linked network of a silasesquioxane based polymer formed from the polymeric hybrid precursors that interpenetrate the polymer.

As used herein a "mixture" can be defined as the state formed by two or more ingredients that do not bear a fixed proportion to one another and that, however commingled, are conceived as retaining a separate existence. As used herein, "mixing" can be defined as a process, operation or technique used to distribute the polymeric hybrid precursor of the present disclosure evenly throughout a polymer. In other words, mixing reduces the nonuniformity of the mixture. Examples of such processes and/or techniques include, but are not limited to, mixing operations that reduce composition nonuniformity of the polymeric hybrid precursor and the polymer. While the mixing process can result in production of a homogeneous product, a somewhat heterogeneous product is within the scope of this disclosure.

The polymer composite matrices of the present disclosure can be suitable for use as a biomaterial and/or in medical devices. The polymer composite matrices of the present disclosure can display excellent performance in many characteristics important for medical device use, including compressive strength, diametral tensile strength, flexural strength, fracture toughness, puncture resistance, hardness, resistance to wear (e.g., characterized by compressive strength and diametral tensile strength), durability, thermal expansion, visual opacity, x-ray opacity, impact strength, chemical durability, electrical conductivity, biocompatibility, modulus, shelf life, patient comfort, ease-of-use, and structural integrity relative to a polymer without the cross-linked network of the polymeric hybrid precursor of the present disclosure.

As provided herein, a mixture of the polymeric hybrid precursor and the polymer can be formed into a desired shape. Once shaped, the polymeric hybrid precursor in the mixture can undergo cross-linking to form a cross-linked network through the polymer. The polymeric hybrid precursor includes chemical linkage moieties that are capable of forming non-covalent bonds with portions of the polymer. This interaction allows the polymeric hybrid precursor to remain mixed (e.g., dispersed through a melting and blending process) in the polymer matrix prior to forming the polymer composite matrix without agglomerating or clumping as could occur with compounds without such non-covalent bonding interactions. Upon processing the polymeric hybrid precursor mixed in the polymer matrix into the desired shape, a sol-gel process can be used to form a cross-linked network with the polymeric hybrid precursor that interpenetrates the matrix of the polymer.

As used herein, a "polymer composite matrix" and/or "polymer composite matrices" refer to a polymer that contains, at least in part, a cross-linked network of a silasesquioxane based polymer formed from the polymeric hybrid precursor of the present disclosure that interpenetrates the polymer and any desired filler and/or adjuvants. The polymeric hybrid precursors and the polymer each include chemical linkage moieties capable of forming non-covalent bonds that allow the components of the polymer composite matrix to be dispersed, as discussed herein. Polymer composite matrices of the present disclosure can be multiple- or one-part compositions, as will be discussed herein.

In addition, the polymer composite matrices of the present disclosure can be further characterized in that it can be substantially insoluble in body fluids and tissues and that is designed and constructed to be placed in or onto the body or to contact fluid or tissue of the body. Ideally, the polymer composite matrices will be biostable, biocompatible, and will not induce reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized; and will substantially maintain its physical properties and function during the time that it remains implanted in or in contact with the body. A "biostable" material is one that is not broken down by the body, whereas a "biocompatible" material is one that is not rejected by the body.

As used herein, a "medical device" can be defined as a device that has surfaces that contact blood or other body fluids and/or tissues in the course of their operation. This can include, for example, extracorporeal devices for use in surgery such as blood oxygenators, blood pumps, blood sensors, tubing used to carry blood and the like which contact blood which is then returned to the patient. This can also include implantable devices such as vascular grafts, stents, electrical stimulation leads, valves for use in the cardiac system (e.g., heart valves), orthopedic devices, catheters, catheter shaft components, filters, guide wires, shunts, sensors, membranes, balloons, replacement devices for nucleus pulposus, cochlear or middle ear implants, intraocular lenses, coatings for such devices, and the like.

Polymeric hybrid precursors mixed in a polymer and polymer composite matrices of the present disclosure can be used in medical devices as well as nonmedical devices. As discussed, they can be used in medical devices and are suitable as biomaterials. Examples of medical devices are listed herein. Examples of nonmedical devices include foams, insulation, clothing, footwear, paints, coatings, adhesives, and building construction materials, besides others.

As used herein, chemical linkage moieties capable of forming a "non-covalent bond" include those linkages that are capable of forming a chemical bond in that allow for non-bonded interactions due to van der Waals, electrostatic, and/or hydrogen bonding forces. For example, chemical linkage moieties capable of forming a "non-covalent bond" include those that can form hydrogen bonds such as, but not limited to, urethane linkages, amide linkages, ester linkages, and combination thereof.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups). In the context of the present disclosure, suitable organic groups for polymeric hybrid precursors of this disclosure are those that do not interfere with the formation of polymer composite matrices.

In the context of the present disclosure, the term "aliphatic group" means a saturated or unsaturated linear or branched hydrocarbon group. This term is used to encompass alkyl (e.g., —$CH_3$, which is considered a "monovalent" group) (or alkylene if within a chain such as —$CH_2$—, which is considered a "divalent" group), alkenyl (or alkenylene if within a chain), and alkynyl (or alkynylene if within a chain) groups, for example. The term "alkyl group" means a saturated linear (i.e., straight chain), cyclic (i.e., cycloaliphatic), or branched monovalent hydrocarbon group including, for example, methyl, ethyl, n-propyl, isopropyl, t-butyl, amyl, heptyl, dodecyl, octadecyl, 2-ethylhexyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. These hydrocarbon groups can be substituted with heteroatoms, which can be in the form of functional groups. The term "heteroatom" means an element other than carbon (e.g., fluorine, nitrogen, oxygen, sulfur, chlorine, etc.).

As a means of simplifying the discussion and the recitation of certain terminology used throughout this disclosure, the terms "group" and "moiety" are used to differentiate between chemical species that allow for substitution or that can be substituted and those that do not so allow for substitution or can not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound, linkage or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

As used herein, the terms "a," "an," "the," "one or more," and "at least one" are used interchangeably and include plural referents unless the context clearly dictates otherwise. Unless defined otherwise, all scientific and technical terms are understood to have the same meaning as commonly used in the art to which they pertain. For the purpose of the present invention, additional specific terms are defined throughout.

The present disclosure relates to a polymeric hybrid precursor that includes at least one silasesquioxane based polymer having a chemical linkage moiety that can form a non-covalent bond with portions of a polymer. As used herein, a silasesquioxane based polymer includes compounds in which silicon atoms are linked to three oxygen atoms and, after undergoing a sol-gel process discussed herein, the oxygen atoms are linked to two silicon atoms. These compounds are of the formula (Formula I):

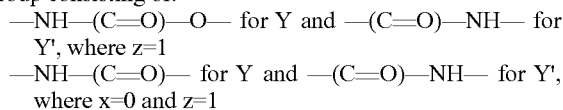

where each $R_1$, $R_2$ and $R_3$ can be the same or different (i.e., is independently) an organic group. Examples of such organic groups include a straight chain or branched alkyl group, a straight chain or branched alkylene group, where each $R_1$, $R_2$ and $R_3$ optionally includes heteroatoms that can be in the chain of the organic group or pendant therefrom as in a functional group. X and z are each independently 0 or 1; m is 1 to 18; and q is 1 to 200. Y and Y' are the chemical linkage moieties that can form a non-covalent bond with a portion of a polymer, where Y and Y' are selected together from the group consisting of:

—NH—(C=O)—O— for Y and —(C=O)—NH— for Y', where z=1

—NH—(C=O)— for Y and —(C=O)—NH— for Y', where x=0 and z=1

—O—(C=O)— for Y and —(C=O)—O— for Y', where z=1
—(NR$_4$)—(C=O)—(NH)— for Y and Y', where z=1; and
—N—[CH$_2$—(CHOH)—CH$_2$—O—R$_3$—Si—(OR$_2$)$_3$]$_2$ for Y and Y', where z=0.

In one embodiment, the values for m, x, and q, and R$_1$, R$_2$ and R$_3$ groups are selected such that the number average molecular weight of a compound of Formula I is suitable to allow for subsequent melt processing with one or more polymers, as discussed herein.

In one embodiment, each R$_1$ is independently a straight chain or branched alkylene group optionally including heteroatoms, such as nitrogen, oxygen, phosphorus, sulfur, and halogen. The heteroatoms can be in the backbone of the R$_1$ or pendant therefrom, and they can form functional groups. Such heteroatom-containing groups (e.g., functional groups) include, for example, an alcohol, carbonyl, ether, acetoxy, ester, aldehyde, acrylate, amine, amide, imine, imide, and nitrile, whether they are protected or unprotected. In one embodiment, R$_1$ does not include heteroatoms. In an additional embodiment, each R$_1$ is independently a straight chain or branched alkylene group includes 18 carbon atoms or less. In a further embodiment, each R$_1$ is independently a straight chain or branched (C2-C8) alkylene group. In other embodiments, each R$_1$ is independently a straight chain or branched (C2-C4) alkylene group (e.g., ethylene, n-propylene, isopropylene, or butylene). In one example, R$_1$ is a C3 alkylene group (propylene or isopropylene).

In an alternative embodiment, when m=1, q=1 and x=0 and R$_1$ can be selected from groups consisting of polypropylene, polyurethane, fluorpolymer (e.g., polytetrafluoroethylene), polyester, polyethylene, polyvinyl chloride, polyamide, and polyimide.

In one embodiment, each R$_2$ and R$_4$ is independently a straight chain or branched alkyl group optionally including heteroatoms, such as nitrogen, oxygen, phosphorus, sulfur, and halogen. The heteroatoms can be in the backbone of R$_2$ and/or R$_4$ or pendant therefrom, and they can form functional groups. Such heteroatom-containing groups (e.g., functional groups) include, for example, an alcohol, carbonyl, ether, acetoxy, ester, aldehyde, acrylate, amine, amide, imine, imide, and nitrile, whether they are protected or unprotected. In one embodiment, R$_2$ and/or R$_4$ do not include heteroatoms. In an additional embodiment, each R$_2$ and R$_4$ is independently a straight chain or branched alkyl group includes 18 carbon atoms or less. In a further embodiment, each R$_2$ and R$_4$ is independently a straight chain or branched (C2-C8) alkyl group. In other embodiments, each R$_2$ and R$_4$ is independently a straight chain or branched (C2-C4) alkyl group (e.g., ethyl, n-propyl, isopropyl, or butyl). In one example, R$_2$ and R$_4$ are each a C2 alkyl group.

In one embodiment, each R$_3$ is independently a straight chain or branched alkylene group optionally including heteroatoms, such as nitrogen, oxygen, phosphorus, sulfur, and halogen. The heteroatoms can be in the backbone of R$_3$ or pendant therefrom, and they can form functional groups Such heteroatom-containing groups (e.g., functional groups) include, for example, an alcohol, carbonyl, ether, acetoxy, ester, aldehyde, acrylate, amine, amide, imine, imide, and nitrile, whether they be protected or unprotected. In one embodiment, R$_3$ does not include heteroatoms. In an additional embodiment, each R$_3$ is independently a straight chain or branched alkylene group includes 18 carbon atoms or less. In a further embodiment, each R$_3$ is independently a straight chain or branched (C2-C8) alkylene group. In other embodiments, each R$_3$ is independently a straight chain or branched (C2-C4) alkylene group (e.g., ethylene, n-propylene, isopropylene, or butylene). In one example, R$_3$ is a C3 alkylene group (propylene or isopropylene).

As will be appreciated, for the formulas herein, R$_1$, R$_2$, and R$_3$ can vary within any one molecule. For example, in addition to each R$_1$, R$_2$, and R$_3$ being the same or different within each [(R$_2$O)$_3$—Si—R$_3$]$_z$—Y—[(R$_1$)$_m$—O$_x$]$_q$—Y'—[R$_3$—Si—(OR$_2$)$_3$]$_z$ group, the (R$_1$)$_m$—O$_x$ groups can be the same or different in any one molecule.

Although certain polymeric hybrid precursors are described herein, the polymeric hybrid precursors used to form the mixture of the polymeric hybrid precursors in the polymer, and the polymer composite matrix of the present disclosure can be formed from a wide variety of compounds having chemical groups that can form chemical linkage moieties capable of forming non-covalent bonds. For example, a method of preparing the polymeric hybrid precursors of Formula I involves the combining of (1) at least one compound of the formula (Formula II) RO$_f$—(C=O)$_i$—[(R$_1$)$_m$—O$_x$]$_q$(C=O)$_n$—O$_e$—R and (2) at least one alkoxy silane containing compound of the formula (Formula III) (R$_2$O)$_3$Si(R$_3$—A) that can react to form the polymeric hybrid precursor of Formula I: [(R$_2$O)$_3$—Si—R$_3$]$_z$—Y—[(R$_1$)$_m$—O$_x$]$_q$—Y'—[R$_3$—Si—(OR$_2$)$_3$]$_z$, as discussed herein.

For the compound of Formula II, i, n, x, e and f are each independently 0 or 1; each R is independently H, an amine (e.g., a primary amine and/or a secondary amine), an isocyanate, or an organic group, R$_1$ is an organic group, as discussed herein, m is 1 to 18, and q is 1 to 200, as discussed herein. For the compound of Formula III, R$_2$ and R$_3$ are each independently an organic group, as discussed herein. Each A is independently a hydroxyl (—OH), an isocyanate, an amine (e.g., a primary amine and/or a secondary amine), or an epoxy compound, selected based upon the value of i, n, e and f, and the group selected for R.

In one embodiment, when R is an organic group it can be a straight chain or branched alkyl group optionally including heteroatoms, such as nitrogen, oxygen, phosphorus, sulfur, and halogen. The heteroatoms can be in the backbone of the R, or pendant therefrom, and they can form functional groups. Such heteroatom-containing groups (e.g., functional groups) include, for example, an alcohol, carbonyl, ether, acetoxy, ester, aldehyde, acrylate, amine, amide, imine, imide, and nitrile, whether they are protected or unprotected. In one embodiment, R does not include heteroatoms. In an additional embodiment, R is a straight chain or branched alkyl group includes 18 carbon atoms or less. In a further embodiment, R is a straight chain or branched (C2-C18) alkyl group. In other embodiments, R is a straight chain or branched (C2-C8) alkyl group (e.g., ethyl, n-propyl, isopropyl, butyl, pentyl, hexyl, hepyl, or octyl). In one example, R is a C2 alkyl group.

Examples of the polymeric hybrid precursor can be prepared from an amine-containing compounds of Formula III where A is either a primary amine (—NH$_2$) or a secondary amine (—(NH)—R), and the compound of Formula II having at least one functional group reactive with the amine group of Formula III, such as an acid, to form an amide for the chemical linkage moiety. In an additional embodiment, one could react the amine group on the compound of Formula III with an anhydride group on the compound of Formula II to make an imide for the chemical linkage moiety. Alternatively, one could react the amine group on the compound of Formula III with an isocyanate group on the compound of Formula II to make a ureylene for the chemical linkage moiety.

In addition, polymeric hybrid precursors can be prepared from a hydroxyl containing compounds of Formula III and the compound of Formula II having at least one functional group reactive with the hydroxyl group of Formula III, such as an acid, to form an ester for the chemical linkage moiety. Alternatively, the polymeric hybrid precursors can be prepared from an amine containing compounds of Formula II (e.g., R is an amine) and the compound of Formula III having at least one functional group reactive with the amine group of Formula II, such as an epoxy compound for A, to form a compound having one or more cabocationic species, such as carbenium ions and/or alkanium ions for the chemical linkage moiety. For example, group A in Formula m can have an epoxy structure, such as

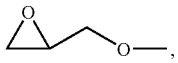

that is reactive with the amine group of Formula II.

Polymeric hybrid precursors can also be prepared from compounds of Formula III, where A is an isocyanate group, and the compound of Formula II having at least one functional group reactive with the isocyanate group of Formula III, such as an alcohol and/or a primary (i.e., —$NH_2$) or secondary amine (i.e., —(NH)—R) to form a urethane and/or a urea for the chemical linkage moiety, Y and Y' in Formula I.

In one example, a urethane- and/or a urea-linkage containing polymeric hybrid precursor of the formula (Formula I): $[(R_2O)_3—Si—R_3]_x—Y—[(R_1)_m—O_x]_q—Y'—[R_3—Si—(OR_2)_3]_x$, where Y and Y' provide the urethane- and/or a urea linkage, are made using an isocyanate-containing compound of Formula III $(R_2O)_3Si(R_3—A)$. It should be understood, however, that a variety of polyols and/or polyamines can be used, including polyester, polyether, and polycarbonate polyols, for example. Furthermore, the polyols and polyamines can be aliphatic (including cycloaliphatic) or aromatic, including heterocyclic compounds, or combinations thereof.

Suitable polyols for use as the compound of Formula II include polyalkylene oxides (e.g., polyethylene oxide and polybutylene oxide), polypropylene ether glycols, polytetramethylene ether glycols (e.g., PTMEG sold under the trade designators "POLYMEG" or "Terathane"), polycaprolactone diols, and polyester polyols (e.g., hydroxyl terminated polyesters obtained from esterification of dicarboxylic acids and diols.

Examples of suitable isocyanate-containing compounds of Formula III $(R_2O)_3Si(R_3—A)$ for preparation of urethane or urea linkage containing polymeric hybrid precursors of Formula I are typically aliphatic monoisocyantes, diisocyantes and triisocyantes, or combinations thereof. In addition to the isocyanate groups they can include other functional groups such as biuret, urea, allophanate, uretidine dione (i.e., isocyanate dimer), and isocyanurate, etc., that are typically used in biomaterials. In one example, the isocyanate-containing metalloid alkoxide can be 3-(triethoxysilyl)propyl isocyanate (Sigma-Aldrich, Milwaukee, Wis.).

The present disclosure further provides methods of forming a mixture of the polymeric hybrid precursors of the present disclosure and a polymer. In one embodiment, methods of forming the mixture can include mixing processes that distribute, incorporate and blend the polymeric hybrid precursors of Formula I into the polymer. Examples of suitable mixing processes include, but are not limited to, the use of a batch mixer, a continuous mixer, a motionless mixer, and a screw extruder (single or twin barrel), among others. Surprisingly, the polymeric hybrid precursors of the present disclosure can undergo melting, either alone or with the polymer, without significant thermal degradation.

As discussed herein, the polymeric hybrid precursors include chemical linkage moieties that can form non-covalent bonds with the polymer that allows them to be miscible with each other. This miscibility would not other wise be possible without the non-covalent bonding interaction of the polymeric hybrid precursors and the polymer as provided herein.

The percentage (% by weight) of the polymeric hybrid precursors to the polymer can be from approximately 0.01% to 10%, from approximately 1% to 10%, from approximately 1% to 5% or from approximately 5% to 10%.

Mixtures of the polymeric hybrid precursors and the polymer can be pelletized and/or formed into a desired shape. In one embodiment, the mixture can be shaped into the desired shape through a molding process selected from the group of blow molding, injection molding, extrusion, casting, coating and fiber spinning. The desired shaped article can then undergo a process to cross-link the polymeric hybrid precursors so as to form the polymer composite matrix of the present disclosure.

The polymeric hybrid precursors of Formula I: $[(R_2O)_3—Si—R_3]_x—Y—[(R_1)_m—O_x]_q—Y'—[R_3—Si—(OR_2)_3]_x$ are capable of forming, either alone or with other precursor compounds (e.g., at least one silasesquioxane based polymer), a cross-linked network of the silasesquioxane based polymer, as discussed herein.

Although certain polymeric hybrid precursors are described herein, the interpenetrating network of the present disclosure can be formed from a wide variety of polymeric hybrid precursors of Formula I. For example, a method of forming the polymer composite matrix involves the forming a mixture of (1) the polymeric hybrid precursors of Formula I with (2) the polymer to form a mixture that can undergo subsequent cross-linking of the polymeric hybrid precursors.

The resulting cross-linked polymeric hybrid precursors interpenetrating the polymer can provide both mechanical and surface properties to the resulting polymer composite matrix. The polymer composite matrix of the present disclosure can combine the advantages of organic polymers (flexibility, low density, toughness, formability) with the excellent mechanical and thermal properties of ceramics (strength, modulus, etc.). In one embodiment, the polymeric hybrid precursors can further be selected such that the polymer composite matrix has the following properties relative to a polymer without the cross-linked polymeric hybrid precursors: greater abrasion resistance, greater lubricity, and/or adding radiopacity to the composite material.

In one embodiment, the polymer composite matrix includes a cross-linked network of the silasesquioxane based polymer (e.g., the polymeric hybrid precursors discussed herein) formed through, for example, a sol-gel process. In one embodiment, the cross-linked network interpenetrates throughout the polymer to form the polymer composite matrix. It has been surprisingly found that sol-gel derived polymer composite matricies can impart superior characteristics to biomaterials. Moreover, it was surprisingly found that sol-gel derived polymer composite matrices can allow the inorganic containing compounds (e.g., the polymeric hybrid precursor of the present disclosure) to be incorporated into polymers at higher levels than is conventional possible.

The Sol-gel process is generally described, for example, in "Sol-Gel Science: The Physics and Chemistry of Sol-Gel Processing" (Brinker et al., Academic Press, 1990). As used herein, "sol-gel" refers to methods of forming the cross-linked network of the silasesquioxane based polymer formed from the polymeric hybrid precursors of Formula I that involves the evolution of inorganic networks through the formation of a colloidal suspension (sol) and gelation of the sol to form a network in a continuous phase (gel).

A wide variety of polymers can be used with the present disclosure in forming the mixture of the polymeric hybrid precursors and the polymer, and the polymer composite matrix. Polymers suitable for use in the mixture and the polymer composite matrix can include those having sufficient strength, hydrolytic stability, and non-toxicity to render them suitable for use in a biological environment. Polymers of the present disclosure in which the polymeric hybrid precursors is to be mixed can be copolymers, random, alternating, block, star block, segmented copolymers (i.e., containing a multiplicity of both hard and soft domains or segments on any polymer chain), or combinations thereof (e.g., where certain portions of the molecule are alternating and certain portions are random). In addition, polymers of the present disclosure can be linear, branched, or crosslinked.

The polymers suitable for forming the polymer composite matrix according to the present disclosure further include, but are not limited to, chemical linkage moieties that have the ability to form non-covalent bonds. Examples of such polymers include those having urethane, ester, amide, imide, urea, carbonate, sulfone, ether, and/or phosphonates linkages, or combinations thereof. Examples of such polymers include polyamide (nylon), polyurethane, polyureas, polyurethaneureas, and/or polyester, among others.

In addition, polymers suitable for forming the polymer composite matrix according to the present disclosure can include both hard and soft segments. As used herein, a "hard" segment is one that is either crystalline (i.e., has ordered domains) at use temperature or amorphous with a glass transition temperature above use temperature (i.e., glassy), and a "soft" segment is one that is amorphous with a glass transition temperature below use temperature (i.e., rubbery). Typically, hard segments add considerable strength and higher modulus to the polymer. Similarly, soft segment adds flexibility and lower modulus, but can add strength particularly if it undergoes strain crystallization, for example. The polymers can vary from hard and rigid to soft and flexible. In one example, the polymers are elastomers. An "elastomer" is a polymer that is capable of being stretched to approximately twice its original length and retracting to approximately its original length upon release.

Suitable polymers can have a viscosity and molecular weights suitable for blending and/or melt processing with the polymeric hybrid precursor discussed herein. In addition to the polymers described herein, the polymer composite matrix of the disclosure can also include a variety of additives. These can include antioxidants, colorants, processing lubricants, stabilizers, imaging enhancers, fillers, and the like. The present disclosure also provides polymers and compounds used to form such polymers, and biomaterials formed from such polymers that can be used in medical devices.

Additional additives can also include, but are not limited to, metal alkoxides $M(OR_2)_m$, where the value for n is dependent on the oxidation state of the metal M. In one embodiment, the metal alkoxides can be incorporated into mixture of the polymeric hybrid precursor and the polymer the prior to the sol-gel process. M can be selected from the group of metals consisting of Groups 2, 4, 5, 8, 9, 13, 14 and 15. For example, M can be selected from the group of metals consisting of Si, Fe, Ti, Zr, Ir, Ru, Bi, Ba, Al, Ta, and Sr. Addition of the additives such as the metal alkoxide can then be used in the sol-gel process to modify the nature of the resulting polymer composite matrix.

Methods of preparing the polymeric hybrid precursors, a mixture of the polymeric hybrid precursors and the polymer, and the polymer composite matrix are also provided. This typically takes place through an end-capping reaction that forms the chemical linkage moieties (e.g., Y and Y') that can form a non-covalent bond with portions of the polymer.

In a typical end-capping reaction, the compound(s) of Formula II, as described herein, and at least one alkoxy silane containing compound of Formula III are combined in the presence of a suitable solvent, and optionally additives to control the chemical and thermal stability of the end-capping reaction. An example of a suitable solvent includes tetrahydrofuran (THF). An example of a suitable additive includes monophenyltriethoxysilane (MPH). The reactions typically take place under reflux conditions (e.g., temperature range of 20 to 80° C.) in an inert atmosphere (e.g., under nitrogen) for a time sufficient for the reaction to come to completion.

Examples of such reactions include reacting butanol (15 ml) with 3-Triethoxysilyl propyl isocyanate (20 ml) in reflux under nitrogen with constant stirring for two hours. The excess butanol was removed and the resulting compound of Formula I was dried in a vacuum oven at 45° C. for 24 hours. In an additional example, Terathane 250 (10.4 g) was reacted with 3-Triethoxysilyl propyl isocyanate (18.5 ml) in reflux under nitrogen for 3 days with constant stirring in THF (10 mL). The THF was then removed and the resulting compound of Formula I was dried in a vacuum oven at 62° C. for 24 hours. In another example, Terathane 650 (15.68 g) was reacted with 3-Triethoxysilyl propyl isocyanate (10.1 ml) in reflux under nitrogen for 2 days with constant stirring in THF (10 mL). The THF was then removed and the resulting compound of Formula I was dried in a vacuum oven at 62° C. for 24 hours. In an additional example, Terathane 1000 (20.68 g) was reacted with 3-Triethoxysilyl propyl isocyanate (8.9 ml) in reflux under nitrogen for 20 hours with constant stirring in THF (10 mL). The THF was then removed and the resulting compound of Formula I was dried in a vacuum oven at 62° C. for 24 hours.

Compounds of Formula I can then be mixed with one or more polymers, as discussed herein. For example, compounds of Formula I illustrated above can be compounded at 5 to 15 weight percent with PEBAX 7033 (a polyamide/polyether/polyester block copolymer) in a Thermo Haake PolyLab Mixer rheometer system having the Rheocord base unit with a RheoMix mixing bowl. In the present example, compounds of Formula I illustrated above are alternately added with the 7033 into the RheoMix mixing bowl and mixed for 2-10 minutes at a speed of 10-20 rpm and a temperature of 195 to 200° C. The resulting compound was then cryoground in liquid nitrogen into particles that passed through a 1 mm mesh screen.

The mixture of the polymeric hybrid precursors and the polymer can then be processed into the desired shape, as discussed herein. For example, particles of the resulting compound discussed above where formed into a film with a Carver Press (Model 3889.002) at 10,000 psi at 205° C. for 3 minutes to produce a film having a thickness of about 0.1 mm. The mixture in the desired shape can then undergo a cross-linking process to form the polymer composite matrix having an interpenetrating network of cross-linked polymeric hybrid precursors throughout the polymer. An example of such a cross-linking process includes the sol-gel process.

Three reactions are generally used to describe the sol-gel process: hydrolysis, alcohol condensation, and water condensation. The characteristics and properties of the interpenetrating network formed throughout the sol-gel process can be related to a number of factors that affect the rate of hydrolysis and condensation reactions, such as, pH, temperature and time of reaction, reagent concentrations, catalyst nature and concentration, aging temperature and time, and drying. Controlling these factors allow for the structure and properties of the sol-gel-derived interpenetrating network formed from the polymeric hybrid precursors to be varied as desired.

A method for preparing the polymer composite matrix for the present disclosure through a sol-gel process involves the combining of (1) the mixture of the polymeric hybrid precursors and the polymer (e.g., in the desired shape) and (2) an aqueous or organic dispersion or sol of reagents that include at least one alcohol and a catalyst provided under conditions for the sol-gel reaction to take place.

Examples of suitable catalysts include mineral acids such as hydrochloric acid (HCl), ammonia, acetic acid, potassium hydroxide (KOH), titanium alkoxides, vandium alkoxides, amines, KF, and HF. Additionally, it has been observed that the rate and extent of the hydrolysis reaction is most influenced by the strength and concentration of the acid- or base-catalyst. In one embodiment, the concentration of the acid- or base-catalyst can be from 0.01 M to 7 M. In addition, the nature of the interpenetrating network can be influenced by the selection of an acid or base catalyst, where under acid-catalyzed conditions the interpenetrating network yields primarily linear or randomly branched polymers which entangle and form additional branches resulting in gelation. On the other hand, interpenetrating network yields derived under base-catalyzed conditions can yield more highly branched clusters which do not interpenetrate prior to gelation and thus behave as discrete clusters.

Examples of suitable alcohols include anhydrous alcohol such as methanol, ethanol, propanol, butanol, pentanol, and mixtures thereof. Suitable alcohols have a water content of less than about 1% by weight, especially less than about 0.5% by weight or less than about 0.1% by weight. Other organic solvent (or mixtures of solvents) can also be used that are miscible with the other components.

In one embodiment, the shaped materials undergoing the sol-gel reaction can have a permeability (i.e., the shaped material has a porosity that allows a liquid or a gas to at least partially penetrate the shaped material) that allows the reagents (e.g., alcohol and/or water) to infiltration the shaped material for the sol-gel reaction to occur. According to the present disclosure, the sol-gel reaction can take place with the reagents in either a liquid phase and/or a gas phase. Typical reaction conditions for the sol-gel reaction can occur in a temperature range of 20° C. to 100° C. Other temperature ranges are also possible.

Such methods are exemplary only. The present disclosure is not limited by the methods described herein for making the compounds of Formula I or the polymer composite matrix derived from the compounds of Formula I.

The invention has been described with reference to various specific embodiments and described by reference to examples. It is understood, however, that there are many extensions, variations, and modification on the basic theme of the present invention beyond that shown in the examples and detailed description, which are within the spirit and scope of the present invention.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A polymeric hybrid precursor comprising a compound of the formula $[(R_2O)_3-Si-R_3-O-CH_2-(CHOH)-CH_2]_2-N-[(R_1)_m-O_x]_q-N-[CH_2-(CHOH)-CH_2O-R_3-Si-(OR_2)_3]_2$, where x is 1; m is 1 to 18; and q is 1 to 200; $R_1$, $R_2$, and $R_3$ are each independently an organic group.

2. The polymeric hybrid precursor of claim 1, where the compound of the formula $[(R_2O)_3-Si-R_3O-CH_2-(CHOH)-CH_2]_2-N-[(R_1)_m-O_x]_q-N-[CH_2-(CHOH)-CH_2-O-R_3-Si-(OR_2)_3]_2$ is derived from at least one compound of the formula (Formula II) $RO_f-(C=O)_i-[(R_1)_m-O_x]_q(C=O)_n-O_e-R$ and at least one alkoxy silane containing compound of the formula (Formula III) $(R_2O)_3Si(R_3-A)$, where i, n, e and f are each independently 0 or 1; x is 1; each R is independently H, an amine, an isocyanate, or an organic group; each $R_1$, $R_2$, and $R_3$ is independently an organic group, m is 1 to 18; and q is 1to 200; and A is independently, an isocyanate, an amine, or an epoxy compound.

3. The polymeric hybrid precursor of claim 1, where $R_2$ is a (C1-C8) alkyl group and each $R_1$ and $R_3$ is independently a (C1-C8) alkylene group.

4. The polymeric hybrid precursor of claim 1, where the compound of the formula $[(R_2O)_3-Si-R_3-O-CH_2-(CHOH)-CH_2]_2-N-[(R_1)_m-O_x]_q-N-[CH_2-(CHOH)-CH_2-O-R_3-Si-(OR_2)_3]_2$ can melt.

5. The polymeric hybrid precursor of claim 1, where the polymeric hybrid precursor can be mixed in a polymer to form a mixture, where the polymeric hybrid precursor includes chemical linkage moieties that can non-covalently bond with portions of the polymer.

6. The polymeric hybrid precursor of claim 5, where the polymeric hybrid precursor mixed in the polymer can be shaped through a molding process selected from the group of blow molding, injection molding, extrusion, casting, coating and fiber spinning.

7. The polymeric hybrid precursor of claim 1, where the compound of the formula $[(R_2O)_3-Si-R_3-O-CH_2-(CHOH)-CH_2]_2-N-[(R_1)_m-O_x]_q-N-[CH_2-(CHOH)-CH_2-O-R_3-Si-(OR_2)_3]_2$ can form a cross-linked network that interpenetrates a polymer using a sol-gel process.

8. A medical device prepared from the polymeric hybrid precursor of claim 1.

* * * * *